United States Patent
Mathisen et al.

(10) Patent No.: US 11,426,266 B2
(45) Date of Patent: Aug. 30, 2022

(54) MEDICAL IMPLANT

(71) Applicant: NOVUS SCIENTIFIC AB, Uppsala (SE)

(72) Inventors: Torbjörn Mathisen, Älvsjö (SE); Anna Wistrand, Vällingby (SE)

(73) Assignee: NOVUS SCIENTIFIC AB, Uppsala (SE)

( * ) Notice: Subject to any disclaimer, the term of this patent is extended or adjusted under 35 U.S.C. 154(b) by 0 days.

(21) Appl. No.: 16/497,039

(22) PCT Filed: Mar. 22, 2018

(86) PCT No.: PCT/EP2018/057238
§ 371 (c)(1),
(2) Date: Sep. 24, 2019

(87) PCT Pub. No.: WO2018/177856
PCT Pub. Date: Oct. 4, 2018

(65) Prior Publication Data
US 2020/0107921 A1    Apr. 9, 2020

(30) Foreign Application Priority Data

Mar. 29, 2017 (SE) .................................. 1750371-5

(51) Int. Cl.
*A61F 2/00* (2006.01)
*A61F 2/12* (2006.01)
*A61L 27/58* (2006.01)

(52) U.S. Cl.
CPC .............. *A61F 2/0063* (2013.01); *A61F 2/12* (2013.01); *A61L 27/58* (2013.01); *A61F 2002/0068* (2013.01); *A61F 2220/0025* (2013.01); *A61F 2250/0029* (2013.01); *A61F 2250/0036* (2013.01)

(58) Field of Classification Search
CPC ....................................................... A61F 2/04
See application file for complete search history.

(56) References Cited

U.S. PATENT DOCUMENTS

| | | | |
|---|---|---|---|
| 8,083,755 B2 | 12/2011 | Mathisen et al. | |
| 8,795,377 B2 * | 8/2014 | Engqvist ............ | A61B 17/8085 623/17.19 |
| 9,566,370 B2 | 2/2017 | Mathisen et al. | |
| 2004/0249464 A1 * | 12/2004 | Bindseil ................ | A61F 2/4455 623/17.16 |
| 2009/0099409 A1 | 4/2009 | Luehrs et al. | |
| 2011/0270391 A1 | 11/2011 | Chitre et al. | |
| 2011/0276134 A1 * | 11/2011 | Manesis .................... | A61F 2/12 623/8 |

(Continued)

FOREIGN PATENT DOCUMENTS

| | | |
|---|---|---|
| EP | 2 915 505 A1 | 9/2015 |
| WO | WO 2011/003422 A1 | 1/2011 |
| WO | WO 2017/050837 A1 | 3/2017 |

*Primary Examiner* — Yashita Sharma
(74) *Attorney, Agent, or Firm* — Foley & Lardner LLP

(57) ABSTRACT

The present disclosure is directed to a degradable medical implant (10) for regeneration of soft tissue, comprising a plurality of scaffolds (1), and a plurality of connecting elements (2), wherein each scaffold (1) has a surface projected in the x-y plane, of maximum 500 mm$^2$, and wherein the connecting elements (2) bind the scaffolds (1) together in the x-y plane.

19 Claims, 2 Drawing Sheets

(56) References Cited

U.S. PATENT DOCUMENTS

| | | |
|---|---|---|
| 2012/0143329 A1 | 6/2012 | Kim |
| 2012/0165957 A1* | 6/2012 | Everland ................. A61L 27/58 623/23.72 |
| 2013/0030360 A1 | 1/2013 | Stopek et al. |
| 2013/0053626 A1 | 2/2013 | Frigstad et al. |
| 2013/0060078 A1 | 3/2013 | Intoccia, Jr. et al. |
| 2014/0081296 A1* | 3/2014 | Palmer ................. A61F 2/0063 606/151 |
| 2014/0171982 A1 | 6/2014 | Marczyk |
| 2014/0228969 A1 | 8/2014 | Engstrnd et al. |

\* cited by examiner

MEDICAL IMPLANT

FIELD OF THE INVENTION

The present disclosure relates to the field of medical technology, in particular to a pliable, degradable medical implant for regeneration of soft tissue. The medical implant comprises a plurality of scaffolds which are connected to each other by a plurality of connecting elements. The medical implant has a mesh-like structure; however the scaffolds provide more void volume for new tissue to regenerate compared to a traditional mesh implant.

BACKGROUND OF THE INVENTION

Degradable polymers like polyesters and polycarbonates have been used for years within the medical device industry as sutures and various fixation devices such as plates, pins and screws to hold small bone fragments together during healing. However, in the field of soft tissue regeneration very few devices have been presented during the past 20 year period. Polymeric meshes are frequently used to reinforce injured or otherwise compromised tissue. These meshes have since their appearance during the 1980's been in frequent use and are still used in large volumes for soft tissue reinforcement. However, since the main material for these meshes has been polypropylene, which is a so-called inert material, and which has been shown to cause a variety of problems such as pain, extrusion, inflammation and late recurrence, to mention a few problems, there is a demand for better material which causes less chronic problems in the patient. Doctors have tested meshes made from degradable polymers such as polyglycolide (DEXON™) and from polyglycolide-co-lactide 90:10 (VICRYL™) but these meshes usually lose their mechanical properties too fast to give a predictable outcome in clinical indications where considerable loads can be found over the impaired site. It was not until 2010 that the first long-term degradable mesh, TIGR Matrix™, was launched to the market, Magnusson et.al. (Hernia, 16(2), 191-7, 2012). The mesh was specially designed to support the load situation during the critical healing period and thereafter to become gradually more compliant to allow for transfer of load onto the newly regenerated tissue to allow for a better remodeling. This mesh is further described for example in U.S. Pat. Nos. 9,566,370 and 8,083,755. Later, the mesh known as PHASIX™ was launched, also made from a degradable material, (poly-γ-hydroxybutyrate), preserving good mechanical properties over a 6-month period just as TIGR Matrix™ as described above. After 3 to 6 months the wound will normally regain about 80% of the uncompromised tissue strength why a 3 to 6 months' period with adequate mechanical strength is considered enough for a mesh that shall be used in clinical indication where it can be exposed to high load situations such as in repair of incisional hernia. Another degradable scaffold that is in frequent use to reinforce and to augment new soft tissue in various clinical indications such as incisional hernia is BIO-A™ which is a sheet like porous scaffold with a thickness slightly less than 2 mm and made from a synthetic copolymer between glycolide and trimethylene carbonate as the main components. The special feature of this scaffold is that it has a larger thickness than the knitted mesh products, such as TIGR Matrixυ, which typically have thicknesses rarely above 0.7 mm. Due to the extra thickness there is a possibility that a thicker layer of new connective tissue can be augmented, which is something often advocated by surgeons using ADM matrices.

The use of degradable meshes/scaffolds to regenerate new connective tissue rather than mesh made from inert material is advantageous in many applications. However, the products currently available in the market have some limitations. Meshes, knitted or weaved, do not possess the thickness required to augment larger/thicker volumes of new tissue and thus achieve the long term stability required to avoid complications. Especially in the area of breast reconstruction where direct implantation of a breast implant is used and the flap tissue can be very thin, the need for a thicker mesh to secure a larger void volume into which new tissue can regenerate is needed to avoid complications such as "bottoming out" after the mesh support has faded due to degradation. BIO-A™ could have been an ideal product for this indication if it had not had such mechanical rigidity; the product cannot be bent into shape like a knitted mesh. TIGR Matrix™ has the perfect drapeability and will nicely adapt to the new breast implant and easy to sew into place, however, due to the height limitation there is probably only a limited volume of new connective tissue that can be regenerated; limited by the thickness of the mesh.

Consequently, there is a need for a mesh-like product that can secure void volume for new tissue regeneration but at the same time is easy to adapt to various underlying tissue structures and also around curved surfaces like those of a breast implant.

SUMMARY OF THE INVENTION

The above objectives are achieved by a plurality of porous scaffolds bound together by connecting elements allowing each individual scaffold to have certain mobility relative to its neighboring scaffolds.

The present disclosure is directed to a degradable medical implant for regeneration of soft tissue, comprising a plurality of scaffolds, and a plurality of connecting elements; wherein each scaffold has a surface area, as projected in the x-y plane, of maximum 500 mm$^2$; and wherein the connecting elements bind the scaffolds together in the x-y plane. The implant thereby has an overall mesh-like structure. The degradable medical implant according to the present disclosure may be described as consisting of one single layer, or alternatively a single-layered structure, made up by the plurality of scaffolds bound together by the plurality of connecting elements.

Preferred embodiments of the present disclosure are described in the dependent claims.

SHORT DESCRIPTION OF THE DRAWINGS

DETAILED DESCRIPTION OF THE INVENTION

The figures illustrate various configurations of scaffolds and medical implants according to the present disclosure. It is to be understood that the figures are schematic drawings only; not necessarily showing correct ratios between the different elements. Further, a medical implant according to the present disclosure can comprise any suitable number of scaffolds and connecting elements. The number and configurations of scaffolds and connecting elements shown in each figure should not be construed as limiting the medical implant to consist of the exact number and configuration of scaffolds and connecting elements shown. The figures should merely be seen as examples of how medical implants can be constructed.

Figure 1:
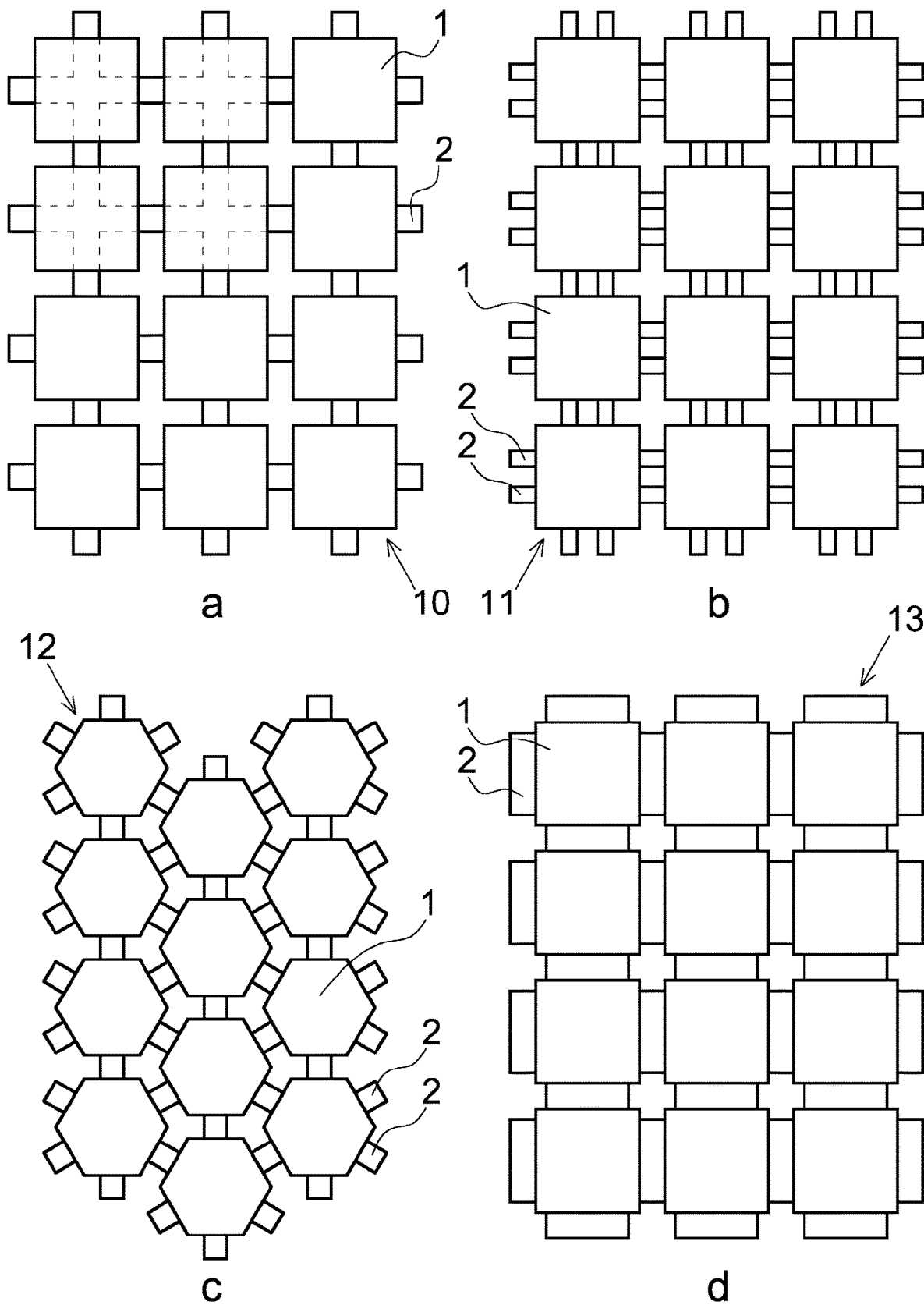
FIG. 1 shows different non-limiting configurations of medical implants according to the present disclosure.

FIG. 1 shows four non-limiting configurations of medical implants according to the present disclosure.

FIG. 1a is a top view depicting a medical implant 10 comprising a plurality of scaffolds 1 and a plurality of connecting elements 2. The upper left part of FIG. 1a illustrates that the connecting elements 2 run through the scaffolds, thus binding the scaffolds into a mesh-like device or medical implant 10. The connecting elements 2 bind the scaffolds 1 together in the longitudinal plane of the mesh-like device, i.e. in the x-y plane of the medical implant 10. The plurality of scaffolds 1 are arranged in a rectangular pattern with a number of scaffolds in each row in the x-direction and a number of scaffolds in each column running in the y-direction. Each connecting element 2 runs through all scaffolds 1 within one row in the x-direction or all scaffolds 1 within one column in the y-direction. Thus, each connecting element 2 which runs through a row of scaffolds in the x-direction intersects each connecting element 2 which runs through a column of scaffolds in the y-direction, and vice versa. The connecting elements 2 intersect inside the scaffolds 1. Each scaffold comprises one connecting element 2 running in the x-direction and one connecting element 2 in the y-direction. The scaffolds 1 have been depicted as quadratic but could equally well have been of any other suitable shape, as described elsewhere herein. All connecting elements 2 in both directions x and y are depicted as monofilaments in FIG. 1a; however they could equally well be made from, but not limited to, non-woven, knitted, or extruded thin film strips, extruded, injection molded or compression molded beams or multifilament structures, or combinations thereof, and can have different cross-sectional shapes, as described in detail elsewhere herein. The medical implant 10 as shown in FIG. 1a contains only 12 scaffolds; however as mentioned above, this number of scaffolds should not be taken as an upper limit for the number of scaffolds which one medical implant can consist of to be useful in the clinical indication it is intended for.

FIG. 1b is a top view depicting a medical implant 11 comprising a plurality of scaffolds 1 and a plurality of connecting elements 2. The connecting elements 2 run through the scaffolds (not shown in the figure), thus binding the scaffolds into a mesh-like device or medical implant 11. The connecting elements 2 bind the scaffolds 1 together in the longitudinal plane of the mesh-like device, i.e. in the x-y plane of the medical implant 11. The plurality of scaffolds 1 are arranged in a rectangular pattern with a number of scaffolds in each row in the x-direction and a number of scaffolds in each column running in the y-direction. Each connecting element 2 runs through all scaffolds 1 within one row in the x-direction or all scaffolds within one column in the y-direction. Thus, each connecting element 2 which runs through a row of scaffolds in the x-direction intersects each connecting element 2 which runs through a column of scaffolds in the y-direction, and vice versa. The connecting elements 2 intersect inside the scaffolds 1. Each scaffold comprises two connecting elements 2 running in the x direction and two connecting elements 2 in the y direction. The scaffolds 1 have been depicted as quadratic but could equally well have been of any other suitable shape, as described elsewhere herein. All connecting elements 2 in both directions x and y are depicted as monofilaments in FIG. 1b; however they could equally well be made from, but not limited to, non-woven, knitted, or extruded thin film strips, extruded, injection molded or compression molded beams or multifilament structures, or combinations thereof, and can have different cross-sectional shapes, as described in detail elsewhere herein. Further, it is to be understood that the number of connecting elements 2 running through each scaffold 1 in one direction could be smaller or larger than two, as long as the total cross-sectional area of the connecting elements 2 running through one scaffold 1 is a maximum of 30% of the surface area of the scaffold side wall, through which the connecting element(s) is/are running, as described in more detail elsewhere herein.

FIG. 1c is a top view depicting a medical implant 12 comprising a plurality of scaffolds 1 and a plurality of connecting elements 2. The connecting elements 2 run through the scaffolds (not shown in the figure), thus binding the scaffolds into a mesh-like device or medical implant 12. The connecting elements 2 bind the scaffolds 1 together in the longitudinal plane of the mesh-like device, i.e. in the x-y plane of the medical implant 12. The connecting elements 2 run through the scaffolds at an angle of 0°, 60° and 120° relative the x- or y-direction, respectively. Due to the hexagonal pattern, each connecting element 2 intersects, within each scaffold, with two other connecting elements 2 running at an angle of 60° and 120°, respectively, relative to the first mentioned connecting element 2. The scaffolds 1 have been depicted as hexagonal but could equally well have been of any other suitable shape, as described elsewhere herein. All connecting elements 2 are depicted as monofilaments in FIG. 1c; however they could equally well be made from, but not limited to, non-woven, knitted, or extruded thin film strips, extruded, injection molded or compression molded beams or multifilament structures, or combinations thereof, and can have different cross-sectional shapes, as described in detail elsewhere herein. Further, it is to be understood that the number of connecting elements 2 running through each scaffold 1 in one direction could be smaller or larger than two, as long as the total cross-sectional area of the connecting elements 2 running through one scaffold 1 is a maximum of 30% of the surface area of the scaffold side wall, through which the connecting element(s) is/are running, as described in more detail elsewhere herein.

FIG. 1d is a top view depicting a medical implant 13 comprising a plurality of scaffolds 1 and a plurality of connecting elements 2. The connecting elements 2 run through the scaffolds (not shown in the figure), thus binding the scaffolds into a mesh-like device or medical implant 13. The connecting elements 2 bind the scaffolds 1 together in the longitudinal plane of the mesh-like device, i.e. in the x-y plane of the medical implant 13. The plurality of scaffolds 1 is arranged in a rectangular pattern with a number of scaffolds 1 in each row in the x-direction and a number of scaffolds 1 in each column in the y-direction. Each connecting element 2 runs through all scaffolds of one row in the x or through all scaffolds 1 of one column in the y-direction. Each connecting element 2 which runs through a row of scaffolds 1 in the x direction intersects each connecting element 2 which runs through a column of scaffolds 1 in the y-direction, and vice versa. The connecting elements 2 intersect inside the scaffolds 1. Each scaffold comprises one connecting element 2 running in the x-direction and one connecting element 2 in the y-direction. The scaffolds 1 have been depicted as quadratic but could equally well have been of any other suitable shape, as described elsewhere herein. All connecting elements 2 in both directions x and y are depicted as strips (e.g. non-woven, knitted or extruded thin film strips) in FIG. 1*d*; however they could equally well be made from extruded, injection molded or compression molded beams, monofilaments or multifilament structures, or combinations thereof, and can have different cross-sectional shapes, as described in detail elsewhere herein.

Figure 2:
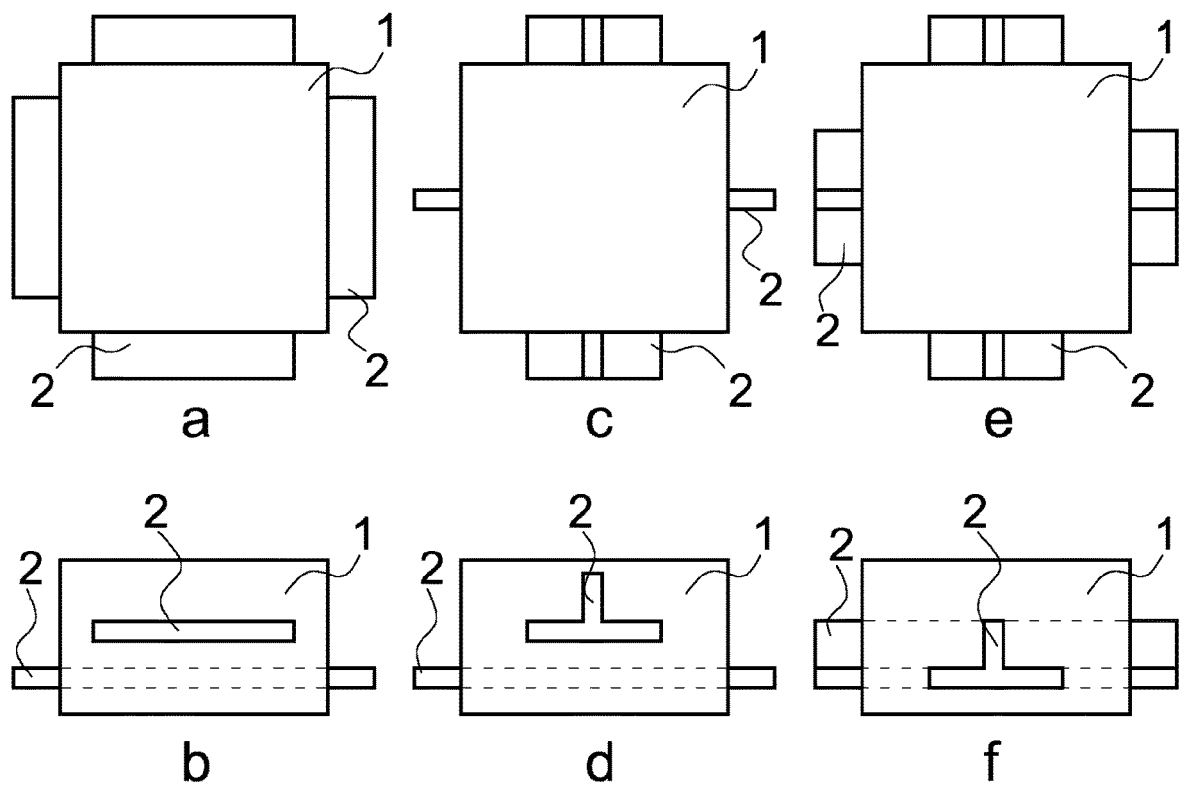
FIG. 2 illustrates different non-limiting configurations of scaffolds and connecting elements according to the present disclosure.

FIG. 2 illustrates three different, non-limiting, configurations of scaffolds and connecting elements according to the present disclosure.

FIG. 2*a* is a top view showing a first configuration of a scaffold 1 and two connecting elements 2. One connecting element 2 runs through the scaffold in the x direction and the other connecting element 2 runs through the scaffold in the y direction. FIG. 2*b* is a cross-sectional side view of the configuration shown in FIG. 2*a*. Here, it can be seen that the two connecting elements 2 run through the scaffold 1 in two different planes in the z direction. The connecting elements 2 are depicted as strips, having a flat, rectangular cross-sectional shape.

FIG. 2*c* is a top view showing a second configuration of a scaffold 1 and two connecting elements 2. FIG. 2*d* is a cross-sectional side view of the same configuration. The one connecting element 2 which runs through the scaffold in the x direction is a monofilament, while the other connecting element 2 which runs through the scaffold in the y direction is in the form of a T-shaped beam. The two connecting elements 2 run through the scaffold 1 in two different planes in the z direction.

FIG. 2*e* is a top view showing a third configuration of a scaffold 1 and two connecting elements 2. FIG. 2*f* is a cross-sectional side view of the same configuration. Each connecting element 2 is in the form of a T-shaped beam. One connecting element 2 runs through the scaffold in the x direction and the other connecting element 2 runs through the scaffold in the y direction. The two connecting elements 2 are running through the scaffold 1 in the same plane in the z-direction. Methods for manufacture of such T-beams crossing each other are described elsewhere herein. It is to be understood that the scaffolds, here depicted as quadratic, could have been of any other suitable shape or any combination thereof, as described elsewhere herein. Likewise, the connecting elements, here depicted as strips in both directions x and y, could equally well be made from extruded, injection molded or compression molded beams, monofilaments or multifilament structures, or any combination thereof, and can have different cross-sectional shapes, as described in detail elsewhere herein.

Figure 3:
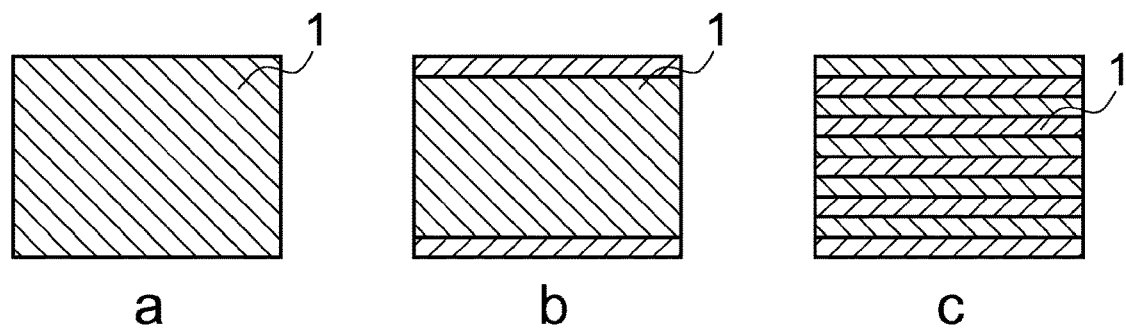
FIG. 3 depicts different non-limiting designs of scaffolds, including different numbers of layers of material.

FIG. 3 illustrates three different, non-limiting, designs of scaffolds. FIG. 3*a* is a side view of a scaffold 1 which has a porous structure. FIG. 3*b* is a side view of a scaffold 1 which is a three layer structure where the different layers can have different properties such as degree of softness. FIG. 3*c* is a side view of a scaffold 1 with 10 layers, which can be made from different materials or different techniques, such as but not limited to electrospinning, knitting, weaving, 3d printing or salt leaching. It is to be understood that the number of layers included in a scaffold, and/or the properties of each layer, can be varied and adapted depending on the intended application. Further, the number of layers per scaffold and/or the properties of each layer can vary across the medical implant.

Figure 4:
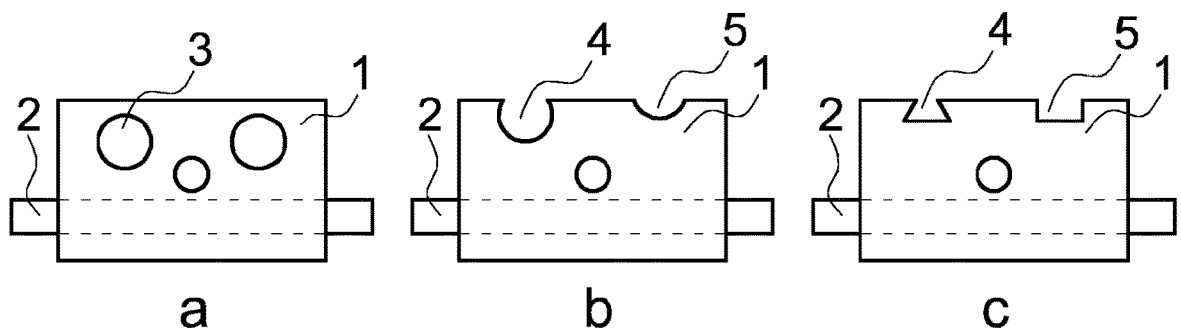
FIG. 4 illustrates different non-limiting designs of scaffolds, including channels, undercuts, and/or grooves or valleys.

FIG. 4 illustrates several possible, non-limiting designs of scaffolds. FIG. 4*a* is a cross-sectional side view of a scaffold 1 and a connecting element 2 in each direction x and y, wherein two open channels 3 are running through the scaffold 1 in the y direction. FIG. 4*b* is a cross-sectional side view of a scaffold 1 and a connecting element 2 in each of directions x and y, wherein a semirounded undercut 4 and a semirounded open groove or valley 5 are running through the scaffold 1 in the y direction. FIG. 4*c* is a cross-sectional side view of a scaffold 1 and a connecting element 2 in each of directions x and y, wherein an angular undercut 4 and an angular open groove or valley 5 are running through the scaffold 1 in the y direction. It is to be understood that a scaffold can contain any combination of channels, undercuts, and/or grooves or valleys. Further, the configuration of the scaffolds with regard to channels, undercuts and/or grooves or valleys may vary across the medical implant, as suitable for the intended application.

Design of Medical Implant

A degradable medical implant according to the present disclosure comprises a plurality of scaffolds linked together by connecting elements running through the scaffolds and thus binding the scaffolds together into a mesh-like medical device, which will be easily adapted to underlying structures such as tissue or medical implants.

The medical implant may attain various shapes, such as round, triangular, quadratic or rectangular to mention a few, in the x-y plane and may have a total projected area in the x-y plane of preferably maximum 1000 cm$^2$, more preferably maximum 600 cm$^2$, which sizes are of interest for applications such as larger abdominal wall reconstruction, suture line reinforcement or even bottom lift procedures. For various breast and prolapse applications the preferred surface area is 300 cm$^2$ or even smaller, while in applications such as a chin implant where the main feature would be to augment soft connective tissue and also in areas where partial mastectomy have been used, the implant size is considerably smaller, preferably in the range of 100 cm$^2$ to only 25 cm$^2$ or even as low as 10 cm$^2$.

In most applications there is no need for any excessive strength in the x-y direction. The strength will be set by the connecting elements as described in more detail elsewhere herein and will depend upon the material used, but also the technique used to manufacture the connecting elements. One important mechanical aspect of the medical implant is the adaptability of the implant to underlying surface and unless the implant has one or more sections which should be ridged to bridge a gap or to keep a certain shape, the medical implant should be easy to bend and in most cases the implant should bend by its own weight. Although not applicable for all variations of medical implants as described herein, the test methodology as described in ASTM D1388 "standard test method for stiffness of fabrics" can be used to define the flexural rigidity of the medical implant. Using the flexural rigidity, the bending modulus shall be calculated as described in Kenkare N et al., "Evaluation of drape characteristics in fabrics", International Journal of Clothing Science and Technology, 17(2): 109-123, 2005. For the purpose of such a test, the height is defined as the height of the connecting element, the width of the medical implant to be tested shall contain at least two rows of scaffolds or the tested width shall be at least 2 cm, and the medical implant shall be in a configuration where the neighboring scaffolds do not interfere with the bending of the medical implant. Under these test conditions, the bending modulus of the implant shall preferably be maximum 10.0 MPa but more preferably maximum 3.5 MPa and even more preferably maximum 1.0 MPa. The above-mentioned configuration where the neighboring scaffolds do not interfere with the bending of the medical implant is important since if two scaffolds are too close to each other and the height is high enough, the lower part of the two neighboring scaffolds will touch and obstruct free bending of the connecting element. Scaffolds Each scaffold is defined by a top surface and a bottom surface, and a number of side walls. The number of side walls and the shape of each side wall depend on the shape of the scaffold. Each of the top surface and the bottom surface can be projected in the x-y plane (herein also said to be in the x-y plane of the scaffold). The x-y plane (i.e. the longitudinal plane) of the scaffolds coincides with the x-y plane of the medical implant. Each of the side walls can be projected in the x-z plane or the y-z plane, respectively, (herein also said to be in the x-z plane or the y-z plane, respectively, of the scaffold). Herein, the term "x-y plane" without further specification is taken to mean a general x-y plane, and it most often coincides with the x-y plane of the scaffolds, as well as the x-y plane of the medical implant. However, it is to be understood that the scaffolds may nevertheless have a top surface or a bottom surface which has a certain inclination to the general x-y plane, and similarly the side walls of a scaffold may have a certain inclination to the general x-z plane or general y-z plane, respectively. Each of the projected area of the top surface, and the projected area of the bottom surface, respectively, is larger than the projected area of any one of the side walls of the scaffold. Each scaffold has a distance to each of its neighboring scaffolds within the range of including from 0.1 to 10 mm but preferably found in the range including from 0.2 to 5.0 mm and even more preferably in the range including from 0.3 to 4 mm. The largest surface, defined as the top or bottom surface, and which can be described by its projected area in the x-y plane of an individual scaffold, is maximum 500 mm$^2$, but is preferably found in the range of including from 25 to 250 mm$^2$ and more preferably within the range of including from 50 to 100 mm$^2$. The height of a scaffold should be in a range of including from 0.5 to 10 mm, preferably including from 1 to 7 mm and more preferably within the range of including from 1.5 to 5 mm. The largest surface, defined as the top surface and/or the bottom surface, respectively, and which can be projected in the x-y plane, can attain any shape such as, but not limited to, rectangular, quadratic, triangular, pentagonal and hexagonal to mention a few. The side walls of the scaffold, each of which can be projected in the x-z or y-z plane, can have an angle relative to the x-y plane within the range of including from −45° to +45°, where the z-direction is defined as 0°.

The scaffold is preferably made with an open porous structure which could consist of one or more layers where the different layers can possess different characteristics such as degree of porosity or mechanical rigidity. It is understood that the scaffolds do not need to be pliable in order for the complete assembly, the medical implant, to be pliable since this feature is achieved by the connecting elements. Preferably, but without limitation, a scaffold consists of 1 to 15 layers. These up to and including 15 layers can be of the same type or different types and also be made with different manufacturing techniques. An example of a scaffold put together with only three layers may be of particular interest to provide a soft surface facing the tissue at both sides of the medical implant and thus minimizing modulus mismatch. In this case the middle layer can be made from a rigid material to hinder scaffold creep or even collapse under pressure from surrounding tissue. Examples of such materials include, but are not limited to, poly-l-lactide, poly-d-lactide, poly-d,l-lactide, polyparadioxanone, polycaprolactone, various tyrosine carbonate polymers, polyorthoesters of various types, poly-γ-hydroxybutyrate or poly-β-hydroxybutyrate. Also any random copolymer between glycolide, l-lactide or d-lactide in combination with themselves or any of the following monomers; trimethylene carbonate, ε-caprolactone and paradioxanone that is characterized by having at least one peak melting temperature above 140° C. as measured by Differential Scanning calorimetry (DSC) using a heating rate of 10° C./min in the first melting of the medical implant. In those cases where the polymer or copolymer is amorphous, the glass transition temperature that is highest on the temperature scale in case of more than one, Tg, shall preferably be found above 37° C. as measured by Differential Scanning calorimetry (DSC) using a heating rate of 5° C./min.

On each side of the rigid middle layer, a softer layer is applied to achieve less modulus mismatch with the surrounding tissue. Preferably these layers can be made from nonwoven techniques producing fine fiber layers such as electrospinning, spun bound, melt blown using softer materials such as those obtained from ABA type copolymers characterized by having a soft core (B) and crystalline arms (A) on both sides of the soft core. These types of polymers can also be made from tri, tetra and multiaxial soft cores using initiators having more than two active initiating sites. Examples of such initiators include, but are not limited to, various molecules, oligomers or polymers having three or more alcohol functions. Such soft core should possess a glass transition temperature below the body temperature 37° C. and more preferably below 25° C. The crystalline arms shall have a melting point above 50° C., preferably above 140° C. A suitable ABA type copolymer is formed by a soft core made from trimethylene carbonate or 1,5-dioxepan-2-one in combination with any monomer known as ε-caprolactone, paradioxanone, lactide (any type) or glycolide. The crystalline arms are made from ε-caprolactone, paradioxanone, l-lactide, d-lactide, glycolide or similar lactone monomers that polymerize via ring opening polymerization, also known as ROP in the literature.

In situations where the medical implant is placed in close contact with a medical device of a different type than described herein or in close contact with bone surface, a two-layered scaffold may be of interest, having a more rigid layer in contact with the medical device or bone surface and a soft layer facing the soft tissue to avoid modulus mismatch.

In most situations the scaffold consists of only one layer made from one material and any of the above materials mentioned can be used to form the scaffold depending on indication of use. A more rigid material in the scaffold or in the middle layer of a tri- or multilayered scaffold will also preserve the open porous structure for a longer period of time which will be determined by the creep in the material or the collapse of the material structure due to the ongoing degradation. However, it is presumed that when tissue invades the porous structure a counteracting force from the new tissue will contribute to an opposite force against structural collapse caused either by creep or degradation. It is well known that different tissues may require different times to grow and repopulate the void space created by the scaffold and it is therefore necessary to use different materials and/or even different designs in different clinical indications. Choosing material that has a high content of glycolide monomers, defined by at least 60% of glycolide monomer or even more preferably more than 75% as mole percentage, will maintain scaffold void volumes for periods of up to 2-5 week depending on processing conditions, and initial molecular weight, to mention some important parameters. Using scaffold materials that have a high content of lactide, defined by at least 70% lactide monomer or even more preferably more than 80% as mole percentage, will maintain scaffold void volume for periods of 1 to 6 months and is preferably used to regenerate tissue with slow tissue growth or when minimal disturbance, during the first wound healing phase and early remodeling phase of the tissue, from leaching degradation products such as hydroxy acids, lactic acid, glycolic acid to mention some, is unwanted.

One suitable method for making the scaffolds would be to 3D print them directly on the connecting element. With 3D printing the connecting element can be placed anywhere in the scaffold and also differently in different sections of the medical implant. 3D printing also allows for individual design scaffolds or scaffolds within a section of the medical implant to achieve different objectives in different sections of the medical implant. One such objective can be to create larger voids for regeneration in certain areas of the implant by varying the height of the scaffolds in different areas of the medical implant. Another objective can be to increase or retard tissue growth in certain areas by having different porosity or intentionally made channels going through one or more of the scaffolds. Such channels preferably have a cross sectional diameter being no more than 0.5 times but more preferably 0.25 times the height of the scaffold. Channels can also be placed on the surface of the scaffolds in which case they are open for tissue ingrowth. Such channels can be designed so that their cross sectional profile is designed to be an undercut. Such undercuts are especially interesting for anchoring of the scaffold and thus the medical implant in the surrounding tissue since the tissue will rapidly grow into the undercuts. The dimension of the opening for channels or grooves found on the surface preferably shall be no larger than 0.3 times the largest cross sectional surface dimension of the scaffold but preferably found in the range of including from 0.3 to 3 mm and more preferably in the range of including from 1 to 3 mm.

Another way of making the scaffold is to place different layers of fabric such as, but not limited to, woven, non-woven or knitted fabrics together and thus achieve the desired height. Bonding of the different layers can easily be accomplished with a glue made from degradable polymer dissolved in a solvent which is applied to the surfaces that shall be bound together without compromising the porosity. Examples of degradable polymers that can be used for bonding would be to use the same polymer as used in the scaffold material and described earlier in this document except for those polymers containing more than 60 mole % of glycolide, paradioxanone or only dissolved in hexafluoroisopropanol. Suitable polymers are those containing any of the different lactide monomers or copolymers thereof in combination with either trimethylene carbonate or ε-caprolactone. Such polymers are dissolved in chloroform, methylene chloride, ethyl acetate, acetone or similar solvents which easily evaporate at normal atmospheric pressure. The solvent needs to be chosen with care since chloroform will dissolve any layer made from polylactide, while ethyl acetate will only dissolve amorphous polylactide such as poly-d,l-lactide. Techniques which can be used to apply the glue include, but are not limited to, spraying or dipping since these techniques are simple techniques that will not hamper the porosity in the fabric. Another technique that can be used to join several layers of fabrics is sewing. Knitted fabrics can be jersey knit utilizing flatbed or circular knitters, but more preferably is fabrics knitted by warp knitting technology since the knitted fabric will not unravel and therefore has a certain integrity higher than jersey knitted fabrics which easily unravels. Non-woven fabrics can be made by for example, but not limited to, the following techniques known as spun-bond, melt blown or electrospinning. All three of these fabrics have different fiber diameter. Of special interest are electrospun layers since the fiber diameter can be varied over a large range, from about 100 nanometers up to a few microns. It is understood that any layer made from any of the aforementioned techniques such as knitting, weaving, electrospinning, spun bound or melt blown can be combined in two or more layers to form a scaffold as characterized earlier herein. Another way of using knitted fabrics is to fold the fabric around the connecting elements to build cylindrically shaped scaffolds.

The scaffold can also be made using well known salt leaching techniques where the salt may be an inorganic salt, organic crystal, polymeric particle, sugar crystal or any combination thereof. Alternatively, a porous structure can be made without using salt leaching technique but involving supercritical carbon dioxide which easily dissolves within the amorphous regions of some degradable polymers such as amorphous polylactides. Releasing the pressure will allow the CO2 to expand to form pores within the polymeric material.

Connecting Element

The connecting elements bind the scaffolds together in the x-y plane (i.e. in the longitudinal plane) of the scaffolds, which is also the x-y plane of the medical implant; such that a mesh-like medical implant is formed. Each connecting element runs through all scaffolds within one row in one direction, or alternatively expressed, each connecting element runs through a number of scaffolds in one direction of the x-y plane. Each connecting element intersects each connecting element which runs through a number of scaffolds in another direction of the x-y plane. All connecting elements intersect each other at any angle of between 0° and 180°. The connecting elements intersect inside the scaffolds, either in different planes in the z-direction, or in the same plane in the z-direction, of the medical implant. Each connecting element can leave or enter a scaffold side wall at an angle of between 0° and 180° to the side wall.

The connecting element is most conveniently made from non-woven strips, knitted strips, extruded thin film strips, extruded beams or monofilament or multifilament structures made from a degradable polymer which is made from any of the monomers lactide, glycolide, paradioxanone, ε-caprolactone, trimethylene carbonate, 1,5-dioxepan-2-one or any combination thereof. The connecting element may also be made from γ- or β-hydroxybutyrate or any combination thereof.

The connecting element can be melt spun, electrospun, spun bound, melt blown, extruded, injection molded, compression molded or otherwise manufactured. Extrusion can be used to form connecting elements having different cross-sectional shapes other than rounded. Examples of such shapes may be rectangular, triangular, in the form of an H-beam or T-beam, to mention a few. The T-beam is preferably, but not limited to, made by extrusion, injection or compression molding. Two T-beams crossing each other in the same plane in the z-direction can be made by injection molding or compression molding. These types of injection molded or compression molded connecting bars can be made porous or equipped with openings.

Strips made from any fabrics as mentioned above are especially interesting as connecting elements as these structures already possess a natural porosity originating from the manufacturing technique itself. These strips of fabric can be made by a plurality of different techniques such as electrospinning, weaving, knitting, melt blown, spunbond to mention a few non-limiting techniques. Where a denser and/or mechanically stronger connecting element is required, tubes made by warp knitting on a machine having double knitting bed is an ideal alternative to strips as described earlier. Another alternative to strips can be a sheet which has been cut in such a way that it resembles strips arranged in a perpendicular pattern. This can be achieved by cutting out squares in a regular pattern on the sheet. When using a sheet instead of strips, the connecting elements are crossing in the same plane inside the scaffold. Using strips as connecting elements, these will cross in different planes inside the scaffolds.

Sheets or strips can also be made from solvent casting and made porous by using salt leaching, phase inversion or laser techniques. When thin strips made from solvent casting or thin film extrusion are used, the thickness should preferably be found within the range 0.05 mm to 2 mm, but more preferably within the range or 0.1 to 1 mm. Such films as described are usually stiffer than the strips made from fabric as described above. Several materials and especially those made from polymers or copolymers containing predominantly lactide monomers can be made pliable, by injection molding, solvent casting or extrusion to mention a few non-limiting techniques.

The cross-sectional area of a connecting element running through a scaffold, alternatively the total cross-sectional area of the connecting elements if more than one connecting element is running through a scaffold, shall be a maximum of 30% of the surface area of the scaffold side wall, through which the connecting element(s) is/are running More preferably the cross-sectional area of the connecting element(s) shall be a maximum of 20% and more preferably a maximum of 15% of the area of the scaffold side wall, through which the connecting element(s) is/are running.

In most areas of soft tissue regeneration, soft and flexible mesh materials are often sought for because of their ability to adapt to the underlying structure. The medical implant according to the present disclosure can easily be made very flexible and/or pliable when the connecting element is made from multifilament, non-woven strips made from melt blown, spun bound or electrospun manufacturing techniques or strips of warp knitted fabric. A more elastic medical implant, with a certain resistance to deformation, can be envisioned when the connecting elements are made from solid beams which can attain various cross sectional shapes or even from monofilaments. The elastic properties of the connecting element can be enhanced by using materials such as those made possible when polymerizing ABA type copolymers with soft core (B) and crystalline arms (A). Such soft core should possess a glass transition temperature below the body temperature 37° C. and more preferably below 25° C. The crystalline arms shall have a melting point above 50° C. but more preferably above 140° C. A suitable ABA type copolymer is formed by a soft core made from trimethylene carbonate or 1,5-dioxepan-2-one in combination with any monomer known as ε-caprolactone, paradioxanone, lactide, glycolide. The crystalline arms are made from ε-caprolactone, paradioxanone, l- or d-lactide, glycolide or similar lactone monomers that polymerize via ring opening polymerization also known as ROP in the literature.

Certain areas of the medical implant can be reinforced by using a more rigid material in the connecting elements, such as, but not limited to, poly-l-lactide, poly-d-lactide, poly-d, l-lactide, polyparadioxanone, polycaprolactone, various tyrosine carbonate polymers, polyorthoesters of various types, poly-γ-hydroxybutyrate or poly-β-hydroxybutyrate. Also any random copolymer between glycolide, l-lactide or d-lactide in combination with themselves or any or the following monomers; trimethylene carbonate, ε-caprolactone and paradioxanone that is characterized by having at least one peak melting temperature above 140° C. as measured by Differential Scanning calorimetry (DSC) using a heating rate of 10° C./min in the first melting of the medical implant. In those cases, where the polymer or copolymer is amorphous, the glass transition temperature that is highest on the temperature scale in case of more than one, Tg, shall preferably be found above 37° C. as measured by Differential Scanning calorimetry (DSC) using a heating rate of 5° C./min.

It is to be understood that any of the connecting elements described above can be combined in a plurality of structures binding the various scaffolds together into being a medical implant having a certain height or volume to allow for tissue augmentation and a certain flexibility allowing the mesh to follow body contours and to create minimal modulus mismatch and tissue friction. Using more rigid connecting elements in certain areas or in the whole medical implant would allow the medical implant to attain a three-dimensional shape which goes beyond the three-dimensional height given to the implant by the height of each individual scaffold. Such implants can be of special interest in the area of breast revision or reconstruction, after mastectomy or in various body sculpturing applications where a certain form of the new tissue is sought for.

Most of the above mentioned techniques to manufacture the scaffolds and/or connecting elements can also be used to deliver natural polymers into the scaffold together with the synthetic degradable materials as listed earlier in this document. Especially, but not limited to, when the scaffolds are made from combining two or more layers that can be made from different materials and/or different techniques, it is easy to also include natural polymer which usually are too mechanically instable to be used on its own. Exceptions from this and which can be of particular interest as one or more layers in the earlier described scaffold would be different forms of decellularized extracellular matrixes (ECM) and in particular acellular dermal matrixes, so called ADM. Electrospinning can be used for combined delivery of synthetic degradable polymers and natural polymers such as collagen so that they are randomly deposited within the same thin sheet of material. This is only an example of a simple technique that can be used to combine synthetic degradable polymers and degradable natural polymers into the same layer which can be used to build up scaffolds and/or connecting elements that can be used in the medical implant described herein. Examples of natural polymers that can be used is, but not limited to, various types of collagen, fibrin, hyaluronic acid, heparin, deactivated heparin, heparan sulphate and the hydrolyzed form of chitin also known as chitosan. The natural polymer is present in the medical implant in a concentration of maximum 90%, more preferably maximum 50% and more preferably maximum 25%.

Most of the above mentioned techniques to manufacture the scaffolds and/or connecting elements can also be used to incorporate various pharmaceuticals which can be of interest for the healing process. Non-limiting examples of such pharmaceutical components are analgesics, antibiotics or other bacteriostatic agents, anti-inflammatory or growth factors to promote various tissue growth or agents that will promote cell differentiations.

The invention claimed is:

1. A degradable medical implant for regeneration of soft tissue, comprising:

a plurality of scaffolds, and a plurality of connecting elements;

wherein each scaffold has a surface area, as projected in an x-y plane, of maximum 500 mm$^2$, wherein the connecting elements bind the scaffolds together in the x-y plane, wherein at least one of the plurality of scaffolds comprises at least two layers of fabric, wherein the connecting elements running in different directions of the x-y plane have different shapes.

2. The medical implant according to claim 1, wherein each scaffold has a distance to each of its neighboring scaffolds, which distance is in a range from 0.1 to 10 mm.

3. The medical implant according to claim 1, wherein the connecting elements run through the scaffolds, thereby binding the scaffolds together into a mesh-like medical implant.

4. The medical implant according to claim 1, wherein each connecting element runs through a number of scaffolds in one direction of the x-y plane.

5. The medical implant according to claim 1, wherein each connecting element intersects each connecting element which runs through a number of scaffolds in another direction of the x-y plane.

6. The medical implant according to claim 1, wherein the connecting elements intersect inside the scaffolds.

7. The medical implant according to claim 1, wherein each scaffold is run through by any number of connecting elements, and the total cross-sectional area of the connecting elements running through the scaffold is a maximum of 30% of the surface area of the scaffold side wall, through which the connecting elements run.

8. The medical implant according to claim 1, wherein each scaffold has a height which is in a range from 0.5 to 10 mm, a range from 1 to 7 mm, or a range from 1.5 to 5 mm.

9. The medical implant according to claim 1, wherein the surface area of each scaffold, as projected in the x-y plane, is in a range from 25 to 250 mm$^2$, or a range from 50 to 100 mm$^2$.

10. The medical implant according to claim 1, wherein the scaffolds comprise a polymer selected from a group consisting of (a) a degradable polymer made from any combination or subcombination of the monomers glycolide, lactide, paradioxanone, ε-caprolactone, trimethylene carbonate, or 1,5-dioxepan-2-one, or any combination or subcombination of such polymers; (b) tyrosine carbonate polymer, polyorthoester of various types, poly-γ-hydroxybutyrate or poly-β-hydroxybutyrate, or any combination or subcombination thereof; or (c) any combination or subcombination of polymers according to (a) and (b).

11. The medical implant according to claim 10, wherein at least some of the scaffolds further comprise a natural polymer or a decellularized matrix.

12. The medical implant according to claim 1, wherein the connecting elements are made from a degradable material made from any combination or subcombination of the following monomers glycolide, lactide, paradioxanone, ε-caprolactone, trimethylene carbonate, 1,5-dioxepan-2-one.

13. The medical implant according to claim 12, wherein at least some of the connecting elements further comprise a natural polymer.

14. The medical implant according to claim 1, wherein the connecting elements have different bending stiffness in different sections of the medical implant.

15. The medical implant according to claim 1, wherein the connecting elements running in different directions of the x-y plane have different mechanical properties.

16. The medical implant according to claim 1, wherein at least one of the scaffolds or at least one of the connecting elements further comprises a pharmaceutically active ingredient.

17. The medical implant according to claim 1, wherein the bending modulus of the implant has a maximum of 10.0 MPa, a maximum of 3.5 MPa, or a maximum of 1.0 MPa.

18. The medical implant according to claim 2 wherein the connecting elements run through the scaffolds, thereby binding the scaffolds together into a mesh-like medical implant.

19. The medical implant according to claim 1, wherein the at least two layers of fabric are glued or sewed to each other.

* * * * *